United States Patent
Kumar

[11] Patent Number: 5,912,124
[45] Date of Patent: Jun. 15, 1999

[54] PADLOCK PROBE DETECTION

[75] Inventor: Rajan Kumar, Plainsboro, N.J.

[73] Assignee: Sarnoff Corporation, Princeton, N.J.

[21] Appl. No.: 08/665,208

[22] Filed: Jun. 14, 1996

[51] Int. Cl.[6] .............................. C12Q 1/68; C07K 21/02; C07K 21/04; C12N 15/00
[52] U.S. Cl. ........................... 435/6; 536/23.1; 536/24.3; 935/76; 935/77; 935/78
[58] Field of Search ................ 435/6; 536/24.3, 536/23.1; 935/76, 77, 78

[56] References Cited

U.S. PATENT DOCUMENTS

| | | | |
|---|---|---|---|
| 5,143,854 | 9/1992 | Pirrung et al. | 436/518 |
| 5,359,115 | 10/1994 | Campbell et al. | 558/110 |
| 5,420,328 | 5/1995 | Campbell | 558/110 |
| 5,424,186 | 6/1995 | Fodor et al. | 435/6 |

FOREIGN PATENT DOCUMENTS

| | | |
|---|---|---|
| WO 92/10092 | 6/1992 | WIPO . |
| WO 93/06121 | 4/1993 | WIPO . |

OTHER PUBLICATIONS

Bardin et al., Histochemistry 100: 387–392 (1993).
Livak et al., PCR Methods and Applications 4: 357–362 (1995).
Landegren et al., Science 241: 1077–1080 (1988).
Matthews et al. Anal. Biochemistry 169: 1–25 (1988).
Agrawal et al., Nucleic Acids Research 18(18):5419–5423 (1990).
The DYNAL Technical Handbook, 2nd Edition, pp. 136–137 (1995).
Lee et al., *Virus Genes*, 9:177–181, 1994.
Nilsson et al., *Science*, 265:2085–2088 (1994).
Walker et al., "The Language of Biotechnology: A dictionary of terms" published by the American Chemical Society (1988).

*Primary Examiner*—W. Gary Jones
*Assistant Examiner*—Ethan Whisenant
*Attorney, Agent, or Firm*—William J. Burke

[57] ABSTRACT

The present invention relates to the detection of a polynucleotide using a padlock probe, whereby a hybridization process is combined with ligation to irreversibly capture polynucleotides of interest. The invention relates both to the padlock probe itself, as well as to methods of use, which allow for varying levels of sensitivity due to amplification of signal processes built into the system. Additionally, preferred formats are disclosed for use of the padlock probes, including the use of microfluidics.

20 Claims, 2 Drawing Sheets

PADLOCK PROBE DETECTION

This invention was made with U.S. Government support under Contract No. 70NANB5H1037. The U.S. Government has certain rights in this invention.

This patent application is being concurrently filed with the following related U.S. patent applications: METHOD FOR POLYNUCLEOTIDE SEQUENCING, R. Kumar and P. Heaney, inventors, Attorney Docket No. DSRC/12024; NUCLEASE PROTECTION ASSAYS, R. Kumar, inventor, Attorney Docket No. DSRC/12038; MICROFLUIDIC METHOD FOR NUCLEIC ACID AMPLIFICATION, Z. Loewy and R. Kumar, inventors, Attorney Docket No. DSRC/12050; METHOD FOR AMPLIFYING A POLYNUCLEOTIDE, Z. Loewy, inventor, Attorney Docket No. DSRC/12081; and AUTOMATED NUCLEIC ACID PREPARATION, D. Southgate and Z. Loewy, inventors, Attorney Docket No. DSRC/12120. This patent application is related to the following copending U.S. patent applications: Ser. No. 60/009,517, filed Nov. 3, 1995, Attorney Docket No. DSRC/11772; Ser. No. 60/006,202, filed Nov. 3, 1995, Attorney Docket No. DSRC/11904; and Ser. No. 60/010,513, filed Jan. 24, 1996, Attorney Docket No. DSRC/11895.

The present invention relates to the field of polynucleotide analysis, and, in particular, to a method for detecting a polynucleotide where a segment of that nucleic acid is known. The present invention further relates to the microfluidic application of the aforementioned method.

There is a continuing need to identify individual polynucleotides in a mixture of polynucleotides. Such individual polynucleotides, once clearly identified, can provide the basis for a medical diagnosis, for example, and allow a physician to prescribe a course of treatment, or recommend against another course of treatment or any treatment. The identification of individual polynucleotides also is important to the conduct of forensic investigations of a crime, where biological matter left at the scene of a crime or on the victim by a perpetrator can be used to connect the identity of the perpetrator with a suspect, simply by analyzing the polynucleotides isolated from the biological matter collected from the crime scene or victim with the polynucleotides taken from a blood sample, for example, from the suspect.

Increasingly, this sort of analysis is conducted with respect to discrete segments of larger polynucleotides that are specifically amplified using conventional techniques, such as the polymerase chain reaction (PCR) or the ligase chain reaction (LCR). The discrete segments are specific indicators of particular diseases or conditions, or are representative segments having a known frequency of presence within the human population, as examples of the use of the amplification methods. While the amplification methods work well for purified target nucleic acid that is present to an appreciable extent, i.e., at least about 100 or more copies per microliter, for example, lesser purifications or exceedingly small amounts of the target nucleic acid tend to lessen the effectiveness of the amplification methods. Exacerbating the decreased effectiveness under such circumstances is the fact that identification of a particular polynucleotide is generally dependent on hybridization between a labeled probe specific for the polynucleotide of interest, and the products of the amplification reaction, also called amplicons. Hybridization is a dynamic process wherein there is an equilibrium between melting and annealing processes. Accordingly, some proportion of the amplicons hybridized by the labeled probe will become free of the probe, thereby lessening the positive signal by which the detection can be made.

Therefore, there is a need for a procedure of detection that potentiates the appearance of a positive signal in detecting an amplicon, or any particular polynucleotide or portion thereof contained in a biological sample, for example. Moreover, there is a need for a detection procedure that irreversibly includes a polynucleotide of interest in the signal by which the polynucleotide of interest is understood to be contained in the biological sample. The present invention answers these needs, as set forth hereinbelow.

SUMMARY OF THE INVENTION

The present invention answers the need for an irreversible capturing of a signal useful in the analysis and detection of polynucleotides. By the use of the probe herein disclosed, a new tool has been devised for the detection of a polynucleotide amidst a mixture of polynucleotides. This design increases the efficiency of detection of a given polynucleotide.

In particular, the present invention relates to a first polynucleotide for identifying a second polynucleotide, the first polynucleotide comprising a ligand attached to each of its termini. Preferably, the first polynucleotide further comprises at least one segment comprising the complement of at least the terminal four nucleotides of each of the 5' and 3' termini of the second polynucleotide, wherein the complements of the 5' terminal nucleotide of the second polynucleotide and the 3' terminal nucleotide of the second polynucleotide that are included in the first polynucleotide are located contiguously to one another. The segment of the first polynucleotide is preferably located at least five nucleotides from either terminus, and can also be located at about its (i.e., the first polynucleotide's) midpoint.

In a preferred embodiment, each ligand attached to the first polynucleotide binds to a solid surface or to a second ligand attached to a solid surface. Such a solid surface, in one embodiment, is a microparticle, wherein the microparticle is preferably paramagnetic. The solid surface alternatively can be flexible and planar, such that a single solid surface is formed into a cylinder or a multiplicity of such solid surfaces are joined and formed into a cylinder.

In another aspect, the invention relates to a method for the detection of a second polynucleotide, comprising:

(A) providing a first polynucleotide, wherein the first polynucleotide comprises:
  (i) a first ligand attached to each of its termini; and
  (ii) at least one segment comprising the complement of at least the terminal four nucleotides of the 5' and 3' termini of the second polynucleotide;

(B) placing the first polynucleotide in contact with the second polynucleotide; and (C) detecting a first-second polynucleotide complex.

Step (A) preferably further comprises contacting the first polynucleotide with a solid surface or a solid surface comprising a second ligand that binds to the first ligands of the first polynucleotide, thereby immobilizing the first polynucleotide. Step (B) preferably further comprises annealing the immobilized first polynucleotide with the second polynucleotide, forming a first-second polynucleotide complex, wherein the second polynucleotide includes a label or a third ligand, wherein the third ligand is recognized by a fourth ligand that includes a label.

The detection method preferably further comprises joining the termini of the second polynucleotide of the first-second polynucleotide complex with a joining agent. The detection method also further comprises washing the first-second polynucleotide complex with a wash fluid, thereby removing unhybridized second polynucleotide.

The ligands used in the context of the present invention, whether with respect to the first, second, third, or fourth ligand, include one or more of biotin, streptavidin, an antigen, an antibody that recognizes the antigen, an amine, or hydrazine, wherein at least one ligand is bound to each of the first polynucleotide and solid surface, which ligands are the same or different. The label used in the context of the present invention is a radioisotope, a fluorescent dye, or a signal-generating enzyme.

The detection method of the present invention is particularly well-suited to detecting a second polynucleotide that is a product of a nucleic acid amplification reaction. Such a detection method preferable include the first polynucleotide having multiple forms wherein each of such forms include different segments that are specific to the complements of at least the terminal four nucleotides of each of the 5' and 3' termini of different second polynucleotides. Preferably, each form of the first polynucleotide is attached to a distinct location on the solid surface.

A preferred embodiment of the present invention entails a method for the detection of a second polynucleotide, comprising:

(A) providing a first polynucleotide, wherein the first polynucleotide comprises:
  (i) a first ligand attached to each of its termini; and
  (ii) at least one first segment comprising the complement of at least the terminal four nucleotides of each of the 5' and 3' or the 3' and 5' termini of a first probe and a second probe, respectively;
(B) providing the first probe comprising a second segment located at one of its termini and having at least four nucleotides of the complement of the second polynucleotide;
(C) providing the second probe comprising a third segment located at one of its termini and having at least four nucleotides of the complement of the second polynucleotide, with the proviso that the second and third segments are different and are the complements of contiguous segments of the second polynucleotide;
(D) contacting the first polynucleotide with a solid surface or a solid surface comprising a second ligand that binds to the first ligands of the first polynucleotide, thereby immobilizing the first polynucleotide;
(E) contacting the first and second probes with a second polynucleotide under conditions that promote hybridization between complementary nucleic acids, forming a probe-second polynucleotide complex;
(F) joining the termini of the hybridized first and second probes of the probe-second polynucleotide complex with a joining agent;
(G) contacting the joined first and second probes with the first polynucleotide under conditions that promote hybridization between complementary nucleic acids, forming a probe-first polynucleotide complex;
(H) joining the termini of the hybridized first and second probes of the probe-first polynucleotide complex with a joining agent;
(I) washing the probe-first polynucleotide complex with a wash fluid, thereby removing unhybridized joined first and second probe; and
(J) detecting the probe-first polynucleotide complex; wherein the first or second probe includes a label or a third ligand, wherein the third ligand is recognized by a fourth ligand that includes a label. In this embodiment, steps (E), (F), (G), and (H) are preferably combined. In another preferred aspect of this embodiment, a denaturation step is employed after step (H) after which steps (E), (F), (G), and (H) are repeated, preferably at least three times, prior to exercising steps (I) and (J).

In another aspect of the method, the first, second, third, or fourth ligand is biotin, streptavidin, an antigen, an antibody that recognizes the antigen, amine, or hydrazine, wherein at least one ligand is bound to each of the first polynucleotide and solid surface, which ligands are the same or different; and wherein the label is a radioisotope, a fluorescent dye, or a signal-generating enzyme. Preferably, the first or second probe, or fourth probe includes the label. The present detection method preferably includes the solid surface that is a paramagnetic microparticle or wherein the solid surface is flexible and planer, such that a single solid surface is formed into a cylinder or a multiplicity of such solid surfaces are joined and formed into a cylinder. Preferably, this method is used to detect the second polynucleotide that is a product of a nucleic acid amplification reaction.

In another preferred the embodiment, the method includes the first polynucleotide having multiple forms, wherein each of such forms include different first segments, and wherein the first and second probes also have multiple forms that include different second and third segments, respectively. The multiple forms of the first polynucleotide are preferably immobilized on the solid surface, wherein the solid surface is one of a group of differentially labeled paramagnetic microparticles or is flexible and planar, such that a single solid surface is formed into a cylinder or a multiplicity of such solid surfaces are joined and formed into a cylinder.

In another aspect, the present invention relates to a method for the combined amplification and detection of a polynucleotide comprising implementing a nucleic acid amplification of a polynucleotide and the aforementioned detection method, wherein the amplification and the detection method are implemented in the same reaction chamber.

DETAILED DESCRIPTION

Figure 1:
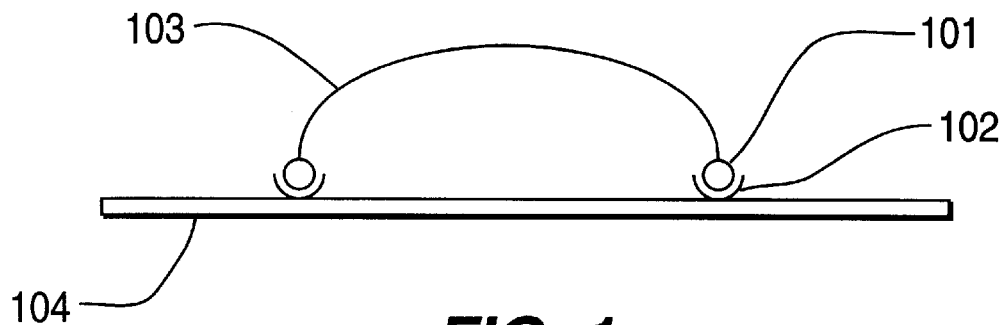
FIG. 1 depicts a schematic drawing of a padlock probe, revealing a method for generating such probes using ligands.

The present invention relates to a method for the detection of a polynucleotide in a mixture of polynucleotides, such as the amplification products of a nucleic acid amplification procedure or a solution of nucleic acid isolated from a biological source. This method is used in the context of benchtop laboratory research, as well as in the conduct of large-scale screening of clinical or forensic samples for the analysis diseases or conditions, or for the analysis of evidence taken from a crime scene. Importantly, this detection method can be used in the context of a microfluidics-based device for automatedly moving fluids in and out of a reaction chamber, which has been disclosed in related copending U.S. Pat. Ser. No. 60/010,513, the contents of which are incorporated herein by reference, and in the context of other procedures that accommodate the analysis and detection of single or multiple polynucleotides of interest.

The present invention is related to the generation of probes that by action of the process of recognizing a polynucleotide of interest concomitantly with the application of a joining agent (which is further explained hereinbelow) irreversibly become entangled in the polynucleotide of interest, in one embodiment, or in a signal amplification second probe in a second embodiment. Such probes have been named "padlock probes," at least in an earlier described circular form. See Nilsson et al., *Science*, 265, 2085–2088 (1994). In the Nilsson et al. reference, circular padlock probes were shown to hybridize with segments of the termini of an oligonucleotide, which termini included sequences that upon such hybridization caused the 3' and 5' ends of the oligonucleotide to abut to one another and be available for joining by a ligase. Because of the helical nature of DNA, circularized probes are wound around the target strand, topologically connecting the probe to target molecules through catenation. The ligation locks the oligonucleotide target to the circular padlock probe.

In the present invention, the concept of the padlock probe is extended. First, the probe is prepared as a linear molecule and presents a circular aspect by virtue of having attached to its termini ligands that bind directly to a solid surface, or indirectly to the solid surface by means of another ligand attached to the solid surface that then binds to the ligand on the probe. One of ordinary skill in the art can synthesize the probe using conventional methods, such as are set forth in *Short Protocols In Molecular Biology* (Frederick M. Ausubel et al., eds. 1992)(hereinafter, Ausubel et al.) and Sambrook et al., *Molecular Cloning, A Laboratory Manual* (2d ed., Cold Spring Harbor Press, Cold Spring Harbor, N.Y., 1989). Different strategies of such synthesis would be evident to a technician; for example, one strategy would entail the separate syntheses of two parts of the probe having a ligand on one terminus only of each, indeed perhaps using the ligand to orient the synthesis, followed by joining the two parts together to form the whole probe. Other strategies could involve splitting the synthesis up further, or straightforwardly synthesizing the probe in toto in a nucleic acid synthesizer.

The probes set forth herein have the aspect of closed circular nucleic acid, by the artifice of attachment of both ends of the probe to a solid surface. One example of such a probe is presented in FIG. 1, wherein a ligand 101 attached to each terminus of the oligonucleotide probe 103 is represented by a circle, and a recognizing ligand 102 attached to the solid surface 104 is represented by the half circle cupped upwards shown embracing the circle ligands. As an example, the circle 101 can represent biotin or an antigen and the half circles 102 can represent, respectively, streptavidin or an antibody that recognizes the antigen; similarly, the half circle cupped upwards embracing the circle, both of which represent ligands, is symbolic of the typically complicated molecular interactions by which ligands recognize each other with specificity. Second, the signal can be potentiated by allowing hybridization to occur in solution between the signal generating probe and the target, and secondly allowing the signal generating probe to be bound by the padlock probe only after having been rendered competent for being so bound. The signal attached to the padlock can be heightened not by the provisioning of multiple hybridizing sequences relative to the termini of the signal generating probe, i.e., referring to FIG. 2, for example, multiple A' B' segments can be included in the padlock probe. In addition, each probe can include multiple labels. Further, the cycles of ligation of the probe to the padlock can be repeated until the signal associated with the padlock is observed.

Figure 2:
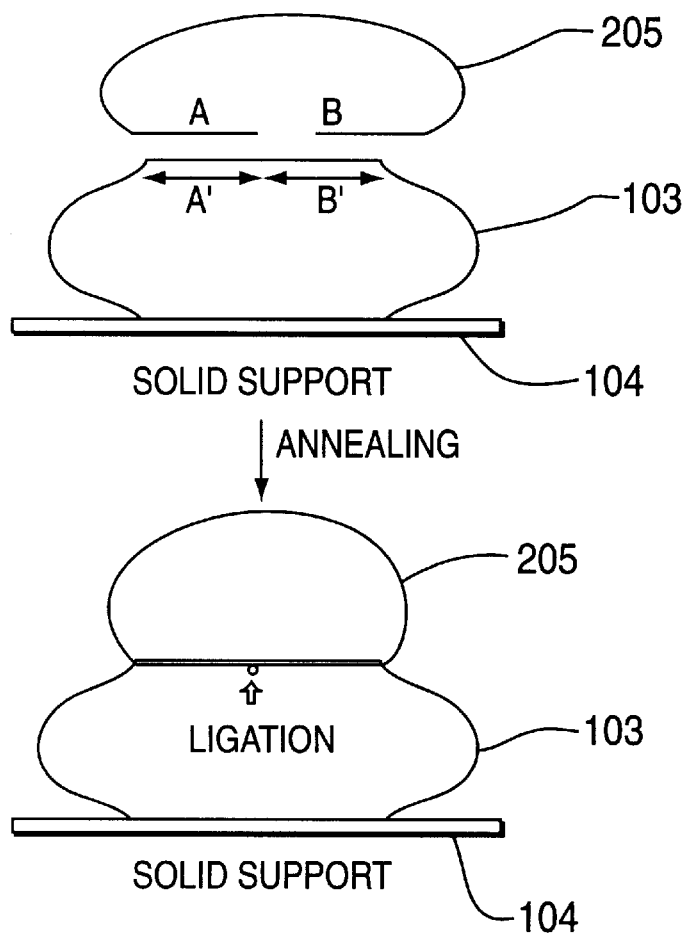
FIG. 2 depicts a schematic drawing of the mechanism by which padlock probes are believed to work.

The basic mechanism by which the present invention is currently believed to work is represented schematically in FIG. 2. The target polynucleotide 205 includes sequences A and B at its respective termini, and the padlock probe 103, attached to a solid surface 104 as demonstrated in FIG. 1, includes among its internal sequences the complement of A and B, which is designated as A' and B'. The positioning of A' and B' is such that the 3' and 5' termini of the target polynucleotide abut to each other upon hybridization to the padlock probe 103. After annealing, ligation is effected either chemically or enzymatically, thereby locking the target polynucleotide onto the padlock probe.

In particular, the present invention relates to a padlock probe, herein referred to as a first polynucleotide, used in the method for identifying a second polynucleotide, where the first polynucleotide comprises a ligand attached to each of its termini. The first polynucleotide preferably includes at least one segment comprising the complement of at least about the terminal four to ten nucleotides of each of the 5' and 3' termini of the second polynucleotide, which is represented by the A' and B' segments in FIG. 2.

More preferably, the segment or segments comprise the complement of at least about the terminal four to seven nucleotides of each of the 5' and 3' termini of the second polynucleotide; most preferably, the segment or segments comprise the complement of at least about the terminal four or five nucleotides of each of the 5' and 3' termini of the second polynucleotide.

Preferably, the complements of the 5' terminal nucleotide of the second polynucleotide and the 3' terminal nucleotide of the second polynucleotide that are included in the first polynucleotide are located contiguously to one another, and, further, are located at least about five nucleotides from either terminus. In one embodiment, the segment is located at about the midpoint of the first polynucleotide. Preferably, the ligand included with the first polynucleotide is any suitable ligand, such as biotin, avidin, streptavidin, an antigen, an antibody that recognizes the antigen, an amine, or hydrazine, among others. A preferred suitable ligand is one that binds specifically to a second ligand, although in certain embodiments, the ligand also or alternatively binds directly to a solid surface. The ligands that are bound to each polynucleotide are preferably the same or different, so long as each ligand attached to the polynucleotide binds to a solid surface or to a second ligand that is itself attached to a solid surface. The solid surface comprises any suitable surface, including but not limited to plastic, glass, cellulose or a cellulose derivative, nylon or other synthetic membranous material, or ceramic.

The solid surface can have any suitable size or shape, including but not limited to that of a microparticle. Indeed, a preferred solid surface is a microparticle, such as a microbead, particularly one that is paramagnetic. Another preferred solid surface is one that is flexible and planar, such that a single solid surface is formed into a cylinder or a multiplicity of such solid surfaces are joined and formed into a cylinder. The first polynucleotide of the present invention is located on the interior or exterior surface of the cylinder.

The first polynucleotide described hereinabove is used in any suitable manner, particularly in the context of the detection of the aforementioned second polynucleotide. Other suitable manners of use include as a probe in a nuclease protection assay, as set forth in the concurrently filed patent application of Kumar, Nuclease Protection Assays, Attorney Docket No. DSRC/12038. Other such uses relate to situations where the polynucleotide must be labeled differentially at the ends, labeled at one end and attached to a solid surface, for example, at the other, and the like.

A first embodiment of the method of such detection comprises (A) providing the first polynucleotide, and (B) contacting the first polynucleotide with a suitable solid surface or a suitable solid surface comprising a second ligand that binds to the first ligands of the first polynucleotide, thereby immobilizing the first polynucleotide. The solid surface and the ligands used in the context of the present detection method are as described hereinabove with respect to the first polynucleotide itself.

The method further comprises (C) contacting the immobilized first polynucleotide with a second polynucleotide under conditions that promote hybridization between complementary nucleic acids, forming a first-second polynucleotide complex, wherein the second polynucleotide includes a label or a third ligand, wherein the third ligand is recognized by a fourth ligand that includes a label. Suitable hybridization conditions are well-known in the art, and can be derived directly from various published sources of molecular biological techniques, such as Ausubel et al., supra, and Sambrook et al., supra The hybridization conditions used are those that will promote substantially only hybridization between perfectly complementary segments of nucleic acid, commonly referred to as highly stringent conditions. The ligands and the labels used with respect to the second polynucleotide include any suitable ligand or label, and are the same ligands and labels used to bind or label any other species set forth in this application. For example, suitable ligands here provide for the specific binding of the second polynucleotide to a particular label, and include, but are not limited to biotin, streptavidin, an antigen, an antibody that recognizes the antigen, Protein A, immunoglobulin, an amine, or hydrazine. The antibody-antigen combination is any suitable one, meaning that the combination exhibits sufficient affinity between the two components that the binding will hold throughout the detection method. Such antibody-antigen combinations include, but are not limited to, such combinations where the antigen is a hapten, a lectin, an immunoglobulin, or any antigenic material for which a sufficiently binding antibody exists or can be generated. Such combinations include those provided commercially by Sigma Chemical Company (St. Louis, Mo.) (hereinafter "Sigma"). Suitable labels provide sufficient signal over noise ratios, for example, when less than about 100 copies of a target nucleic acid are present per microliter in a sampling; such suitable labels include a radioisotope, a fluorescent dye, or a signal-generating enzyme. Suitable radioisotopes include, but are not limited to, $^3$H, $^{14}$C, and $^{32}$P. Suitable fluorescent dyes include, but are not limited to, fluorescein, rhodamine, 7-amino-4-methylcoumarin, dansyl chloride, Cy3, Hoechst 33258, R-phycoerythrin, Quantum Red™, Texas Red, suitable analogs and derivatives thereof, and the like. Suitable signal-generating enzymes include, but are not limited to, alkaline phosphatase, peroxidase, and urease. Any of the aforementioned labels can be obtained commercially, such as from Sigma. Preferably, at least one ligand is bound to each of the first polynucleotide and solid surface, which ligands are the same or different; and at least one label is bound to the second polynucleotide or fourth ligand.

The method preferably further comprises (D) washing the first-second polynucleotide complex with a suitable wash fluid, thereby removing unhybridized second polynucleotide. Such wash fluids are set forth in Ausubel et al. and Sambrook et al. and typically include a buffer for maintaining about a neutral pH, such as Tris, a chelator, such as EDTA, and detergent, such as sodium dodecyl sulfate (SDS). Thereafter, or prior to, the method includes step (E), which is directed to joining the termini of the second polynucleotide of the first-second polynucleotide complex with a suitable joining agent, using conventional methods, such as is set forth in Ausubel et al. and Sambrook et al.; and, ultimately, step (F), for detecting the first-second polynucleotide complex, again using conventional methods, as set forth in Ausubel et al. and Sambrook et al. A suitable joining agent of step (E) is a chemical or an enzyme that will specifically bind abutting 3' and 5' ends of two contiguous polynucleotides, and is preferably cyanogen bromide, carbodiimide, or ligase. See Ausubel et al., Rubin et al., *Nucleic Acids Res.*, 23, 3547–3553 (1995); and Ng and Orgel, *Nucleic Acids Res.*, 15, 3573–3580 (1987).

The method of the present invention preferably includes use of a solid surface that comprises plastic, glass, cellulose or a cellulose derivative, nylon or other synthetic membranes, ceramic, or any other suitable material. A preferred solid surface has the shape of a microparticle, particularly a microparticle that is paramagnetic. Another preferred embodiment includes a solid surface that is flexible and planar, such that a single solid surface is preferably formed into a cylinder or a multiplicity of such solid surfaces are preferably joined and formed into a cylinder. When the inventive method includes the cylindrical solid surface, the first polynucleotide is preferably on the interior or exterior surface of the cylinder; the first polynucleotide can also be on both the interior and exterior surfaces of the cylinder. The present method involving a cylindrical solid surface preferably comprises rotating the cylinder to permit all surfaces containing the immobilized first polynucleotide to come into contact with the second polynucleotide, wash fluid, or joining agent of step (C), (D), or (E).

The present method is particularly well-suited for the detection of a second polynucleotide that is a product of a suitable nucleic acid amplification reaction, which products are also referred to as amplicons. Such suitable reactions, standard procedures of which are noted by reference, include the following: Polymerase chain reaction (PCR; see, e.g., U.S. Pat. 4,683,202 and Ausubel et al. at Unit 15.1; ligase chain reaction (LCR; see, e.g., European Patent Publication 320,308 and Schachter et al., *J. Clin. Microbiol.*, 32, 2540–2543 (1994)); strand displacement amplification (SDA; see, e.g., Walker et al., *PCR Methods and Applications*, 3, 1–6 (1993)); nucleic acid sequence-based amplification (NASBA; see, e.g., van Gemen et al., *J. Virol. Methods*, 43, 177–188 (1993)); and transcription-based nucleic acid amplification (e.g., see U.S. Pat. 5,194,370 and U.S. Pat. 5,215,899). The first two amplification procedures, the PCR and LCR methods, both relate to amplification of DNA segments, and are commonly used in methods of detection and analysis of such segments. These procedures conventionally are used with thermal cyclers for generating cycling denaturing-renaturing/reaction temperatures for the reaction. The other three amplification procedures, the SDA, NASBA, and other transcription-based nucleic acid amplifications, also can be used to amplify a DNA segment, but provide RNA amplification products. Typically, these procedures require at least an initial high temperature incubation to provide for the melting of the target DNA upon or prior to the adding of primer, after which the reactions are conducted isothermally at a lesser temperature. For example, the published NASBA procedure includes an initial incubation at 65° C. followed by incubations at 41° C. Similarly, the SDA procedure referenced above includes an initial incubation at 95° C. followed by incubations at 37° C.

For detecting more than one second polynucleotide at a time, the present method preferably can be used where the first polynucleotide has multiple forms, wherein each of such forms preferably include different segments that are specific to the complements of at least about the terminal four nucleotides of each of the 5' and 3' termini of different second polynucleotides. The present method is well-suited to such multiple detection schemes by attaching each form of the first polynucleotide to a distinct location on the aforementioned solid surface. When multiple forms of the first polynucleotide are immobilized on the solid surface, the solid surface is preferably flexible and planar, such that a single solid surface is formed into a cylinder or a multiplicity of such solid surfaces are joined and formed into a cylinder. The cylindrical solid surface is then utilized as described above, wherein the first polynucleotide is on the interior or exterior surface of the cylinder and, with respect to steps (C), (D), and (E), the cylinder is preferably rotated to permit all surfaces containing the immobilized first polynucleotide to come into contact with the second polynucleotide, wash fluid, or joining agent.

Figure 3:
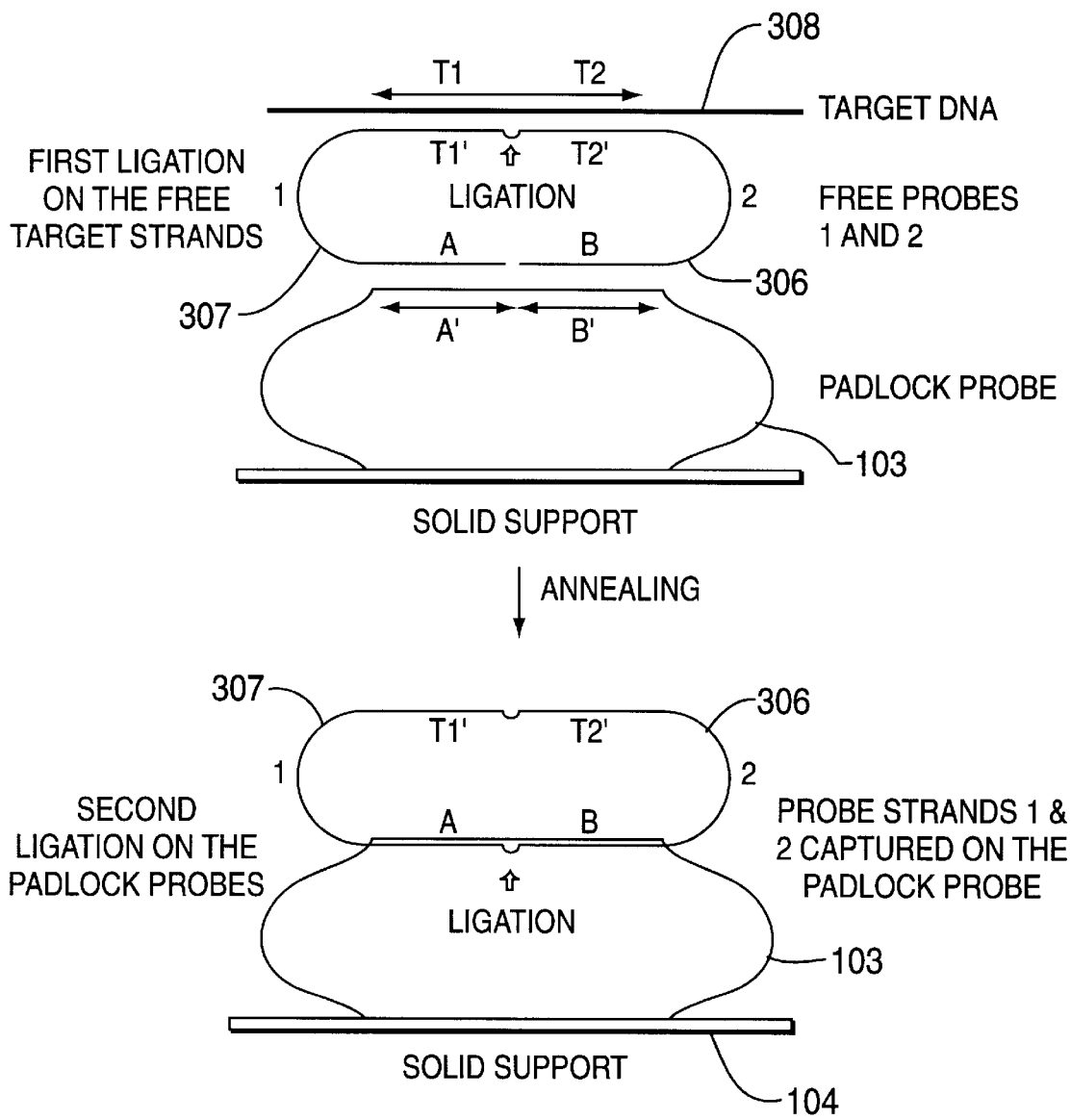
FIG. 3 depicts a schematic drawing of the mechanism by which padlock probes are believed to work, wherein there is signal amplification and no direct hybridization between the padlock probe and the target nucleic acid.

Another embodiment of the present invention incorporates signal amplification into the padlock probe design, which is believed to work in accordance with the schematic drawing of FIG. 3. The target polynucleotide 308, a DNA as shown in the FIG. 3 but could be an RNA instead, includes a segment of the molecule represented by "T1," which is contiguous with a second segment of the molecule represented by "T2." Two free probes, 307 and 306 respectively, are constructed for this detection scheme, namely probe 1, having one terminus that includes the complement to T1, labeled "T1'," and a second terminus that includes segment A, and probe 2, having one terminus that includes the complement to T2, labeled "T2'," and a second terminus that includes segment B. This embodiment also includes, of course, a padlock probe 103 as described above, referred to herein as the first polynucleotide, which, as exemplified in FIG. 3, includes the complement to segments A and B, labeled "A'," and "B'."

In this signal amplification embodiment, the target polynucleotide 308 and the two free probes (307 and 306) are placed into contact with one another under conditions that promote hybridization. The free probes hybridize such that the 5' end of one of them is directly juxtaposed to the 3' of the other, allowing a ligation reaction mediated by a joining agent to join them together. The free probes are, accordingly, joined on one end, but still free on the other, forming a linear molecule. Thus, the target polynucleotide is free to disassociate from the free probes. Because this first step takes place entirely in solution, under appropriate conditions the process favors the hybridization and ligation, thus potentiating the number of free probes joined by the T1' and T2' termini.

The remaining free ends of the free probes are available to anneal to the A'B' segment of the padlock probe; upon doing so, a ligation of the 3' and 5' ends of the combined free probes causes the combined probe 1 and 2 construct to become irreversibly entangled with the padlock probe. The amplification of signal in this process arises from two sources: First, multiple labels can be attached to the free probes in a manner that should have little or no impact on the hybridization and ligation processes. Second, the second step of annealing and permanent entanglement in the padlock probe can be repeated successively until little or no more signal is added to the padlock probes, or until the padlock probes have captured sufficient signal for appropriate interpretation.

In particular, the second embodiment relates to a method for the detection of a second polynucleotide, wherein the first (i.e., the padlock probe) and second polynucleotides do not hybridize directly to one another, comprising:

(A) preferably providing a suitable first polynucleotide, wherein the first polynucleotide comprises:
  (i) a suitable first ligand preferably attached to each of its termini; and
  (ii) at least one suitable first segment (for example, A' and B' of FIG. 3) preferably comprising the complement of at least about the terminal four to ten nucleotides of each of the 5' and 3' or the 3' and 5' termini of a first probe and a second probe, respectively; more preferably, at least about the terminal four to seven nucleotides; most preferably, at least about the terminal four or five nucleotides;

(B) preferably providing the first probe comprising a second segment (e.g., T1' of FIG. 3) located at one of its termini and having at least about four to about ten nucleotides of the complement of the second polynucleotide; more preferably, at least about the terminal four to seven nucleotides; most preferably, at least about the terminal four or five nucleotides;

(C) preferably providing the second probe comprising a third segment (e.g., T2' of FIG. 3) located at one of its termini and having at least about four to about ten nucleotides of the complement of the second polynucleotide; more preferably, at least about the terminal four to seven nucleotides; most preferably, at least about the terminal four or five nucleotides; with the proviso that the second and third segments are preferably different and are the complements of contiguous segments of the second polynucleotide;

(D) preferably contacting the first polynucleotide with a suitable solid surface or a suitable solid surface comprising a suitable second ligand that binds to the first ligands of the first polynucleotide, thereby immobilizing the first polynucleotide;

(E) preferably contacting the first and second probes with a suitable second polynucleotide (i.e., the target nucleic acid) under suitable conditions that promote hybridization between complementary nucleic acids, as referred to hereinabove, forming a probe-second polynucleotide complex;

(F) preferably joining the termini of the hybridized first and second probes of the probe-second polynucleotide complex with a suitable joining agent, such as, but not limited to, cyanogen bromide, carbodiimide, or ligase;

(G) preferably contacting the joined first and second probes with the first polynucleotide under suitable conditions that promote hybridization between complementary nucleic acids, forming a probe-first polynucleotide complex;

(H) preferably joining the termini of the hybridized first and second probes of the probe-first polynucleotide complex with a suitable joining agent, such as, but not limited to, cyanogen bromide, carbodiimide, or ligase;

(I) preferably washing the probe-first polynucleotide complex with a suitable wash fluid, thereby removing unhybridized joined and free first and second probes; and (J) preferably detecting the probe-first polynucleotide complex; wherein the first or second probe includes a suitable label or a suitable third ligand, wherein the third ligand is preferably recognized by a suitable fourth ligand that includes a label. Multiple labels and third-fourth ligands can be employed, which serves to increase the signal per target nucleic acid identified by the method. Of course, one of ordinary skill will readily perceive that steps (E), (F), (G), and (H) can be combined. Of greater note to the amplification capabilities of the method, a denaturation step can be employed after step (H), after which steps (E), (F), (G), and (H) would be repeated, resulting in the capturing of joined probes 1 and 2 that were not captured in the previous exercise of steps (E) to (H) by the padlock probe, i.e., the first polynucleotide. Preferably, the denaturation step after step (H) followed by steps (E), (F), (G), and (H) are repeated at least three times prior to exercising steps (I) and (J).

The denaturation step can be accomplished thermally, chemically, enzymatically, electrostatically, or any combination thereof. Thermal denaturation is well known in the art, and is well-described by Ausubel et al., supra. The inventive method is readily adapted to either using a standard thermal denaturation of heating the polynucleotides of interest to 90° C. to 100° C., or using lesser degrees of heat in the presence of formamide, which serves to reduce the melting temperature of duplex nucleic acids. Chemical denaturation can be accomplished using base, and is well described in the concurrently filed Loewy and Kumar patent application, Attorney Docket No. DSRC/12050, which is incorporated herein by reference. Enzymatic denaturation is also well known in the art, commonly employing an enzyme from the class of enzymes known as helicases, which in the presence of riboATP is known to denature DNA, for example. The reaction conditions suitable for separating the strands of nucleic acids with helicases are described by Kuhn et al., in *Cold Spring Harbor Symposia on Quantitative Biology*, Vol. XLIII, 63–67 (1978). Electrostatic denaturation can also be employed in the context of the present invention, which is well described in the aforementioned concurrently filed Loewy and Kumar patent application.

Suitable ligands preferably used in the context of the present invention were described above, as were suitable labels. More than one ligand is used for the present method, preferably between about one and about four, depending on the embodiment; the same or different ligands are used as described. Single or multiple labels are used in the context of the present invention, which labels can be the same or different. With respect to the second embodiment, it is important to point out that label can be attached with the first or second probe, including, of course, both, and that the fourth ligand can be attached to a label, instead or in addition to the other labels. The suitable solid surface in the second embodiment is no different than the prior discussion of preferred solid surface descriptions, including the setting forth of paramagnetic microparticles and cylindrically formed surfaces as preferred solid surfaces, as well as the methods of using same. Further, the second embodiment, as well as all other embodiments of the invention, is contemplated to be used in any application where the detection of a particular polynucleotide is desired, or where the detection of a particular group of polynucleotides is desired. For example, it is desirable to detect the expression of a gene or a group of genes known to be expressed in a particular cell type, thereby providing a valuable tool for the analysis of metastasized cancer, for example. Accordingly, the second polynucleotides can be a mixture of mRNA isolated from particular cells or tissue. In forensic analysis, assessment of the presence of different nucleic acid sequences having known frequencies of presence in the population can be accomplished readily with the present invention, using a microfluidics or cylindrical solid surface approach, for example. For these analytic purposes, it is contemplated that the inventive method will be used in the context of analyzing amplicons derived using any suitable nucleic acid amplification reaction, as discussed hereinabove.

For such analysis of the presence of any of a group of polynucleotide sequences in an individual, or a biological sample taken from an individual or any other source, the first polynucleotide preferably has multiple forms, wherein each of such forms include suitable different first segments, and wherein the first and second probes also have multiple forms that include different suitable second and third segments, respectively. The multiple forms of the first polynucleotide are preferably immobilized on the aforementioned solid surface, wherein the solid surface is flexible and planar, such that a single solid surface is formed into a cylinder or a multiplicity of such solid surfaces are joined and formed into a cylinder; alternatively, the multiple forms of the first polynucleotide are attached to different suitable solid surfaces, such as microparticles, which are differentially labeled using the labels set forth herein or any other suitable label.

Further preferred embodiments of the present invention include the method of combining amplification and detection of a polynucleotide, which comprises implementing a nucleic acid amplification of a polynucleotide and the one of the embodiments of the method of detection set forth hereinabove, wherein the amplification and the method are implemented in the same reaction chamber. Accordingly, with respect to the first embodiment of the inventive method discussed above, the method would further comprise adding a suitable nucleotide polymerase prior to step (E), which is directed to joining the termini of the second polynucleotide of the first-second polynucleotide complex with a suitable joining agent.

Methods of synthesizing nucleic acid probes are well known in the art. Such methods are reviewed for example in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in *Design and Targeted Reaction of Oligonucleotide Derivatives*, CRC Press, Boca Raton, Fla, pages 100 et seq. The phosphoramidite and phosphite triester approaches are most broadly used, but other approaches include the phosphodiester approach, the phosphotriester approach and the H-phosphonate approach.

Methods of attaching labels (i.e., reporter molecules) to polynucleotides are also well known in the art. For instance, Biosearch Products of PerSeptive Biosystems (Framingham, Mass.) markets 5' linker groups that are compatible with phosphoramidite chemistry. One of these groups includes a six-carbon spacer and a terminal amine that is protected with a trifluoroacetyl ("TFAc"). The TFAc protecting group is base-label and is removed during the normal post-synthesis workup of an oligonucleotide synthesized by the phosphoramidite method, which workup involves hydrolysis in the presence of ammonium hydroxide. Another amine-containing linker from this company also has a six-carbon spacer group and has the amine protected with a methoxytrityl ("MMT") group. The MMT group is acid-label, requiring a separate deprotection step. Both of these amine linkers can be used to attach molecules such as biotin or fluorescein. These amine spacer groups can also be used to attach other molecules having a free acid that can be used to form an amide with the amine group through a condensation reaction. Another linker from Biosearch Products has a six-carbon spacer with a thiol group protected by a trityl group. The trityl protecting group is removed by treatment with silver nitrate and dithiothreitol. This linker can be used to attach enzymes and molecules that incorporate maleimide. Methods to couple multiple labels can include the attachment of a polymer having a number of reactive sites, such as a number of amino or thiol groups, which reactive sites can be used to attach label. Labelling methods are described in: Sinha and Striepeke, "Oligonucleotides with Reporter Groups Attached to the 5' Terminus" in Oligonucleotides and Analogues: A Practical Approach, Eckstein, Ed., IRL, Oxford, 1991, p. 185 et seq.; Sinha and Cook, "The Preparation and Application of Functionalized Synthetic Oligonucleotides: 3. Use of H-Phosphate Derivatives of Protected Amino-Hexanol and Mercapto-Propanol or Mercapto-Hexanol," Nucleic Acids Research, 1988, Vol. 16, p. 2659 et seq.; Haugland, Molecular Probes Handbook of Fluorescent Probes and Research Chemicals, Molecular Probes, Inc., Eugene, Oregon., 1992, p. 20 et seq.; Theisen et al., "Fluorescent Dye Phosphoramidite Labelling of Oligonucleotides," Tetrahedron Letters, 1992, Vol. 33, p. 3036 et seq.; Rosenthal and Jones, "Genomic Walking and Sequencing by Oligocassette Mediated Polymerase Chain Reaction," Nucleic Acids Research, 1990, Vol. 18, p. 3095 et seq.; Smith et al., "The Synthesis of Oligonucleotides containing an Aliphatic Amino Group at the 5' Terminus—Synthesis of Fluorescent DNA Primers for Use in DNA-Sequence Analysis," Nucleic Acids Research, 1985, Vol. 13, 2399 et seq.

In many of the applications of the methods described herein, it is useful to have an array having unique nucleic acid probes at each of a multitude of separate locations. One way to form such an array is to manufacture the nucleic acid probes using the liquid distribution system described by Zanzucchi et al. in "Liquid Distribution System," PCT/US95/14590, a PCT application filed Nov. 9, 1995. That liquid distribution system can conduct distinct synthesis in a great number of separate reaction wells, such as 10,000 reaction wells. The synthesis in each reaction well can occur on a bead or microparticle or can occur on the surfaces of the wells, where these surfaces have been appropriately treated. The wells are formed on a plate that is separable from the portions of the liquid distribution system used to shuttle reagents to a multitude of reaction wells. Accordingly, the device can be used to synthesize separate oligonucleotides bound to the solid support in each of the reaction wells. The plate can then be subjected to the nuclease protection methodology described herein. This PCT/US95/14590 patent application and corresponding U.S. application No. 08/556,036, filed Nov. 9, 1995 are incorporated herein in their entirety by reference.

Another way of forming an array having distinct nucleic acid probes at a multitude of distinct sites is to apply the photolithographic synthesis procedures described in a number of patents and patent applications owned by Affymax, Inc. These include Fodor et al., "Very Large Scale Immobilized Polymer Synthesis," W092/10092; Dovor et al., "Method of Synthesizing Diverse Collections of Oligomers," W093/06121; Campbell et al., "Methods for Synthesis of Phosphonate Esters," U.S. Pat. No. 5,359,115; Campbell, "Methods for Synthesis of Phosphonate Esters," U.S. Pat. No. 5,420,328; Fodor et al., "Very Large Scale Immobilized Polymer Synthesis," U.S. Pat. No. 5,424,186; and Pirrung et al., "Large Scale Photolithographic Solid Phase Synthesis of Polypeptides and Receptor Binding Screening Thereof," U.S. Pat. No. 5,143,854.

Of course, the array can be simply constructed by spotting the nucleic acid probes onto an appropriate adsorptive surface such as a nylon filter, a nitrocellulose filter, polycarbonate, polystyrene or another plastic. Alternatively, the array can be constructed on commercial arrays having reactive surfaces to which nucleic acid probes can be covalently coupled. For example, Nunc, (Naperville, Ill.) sells an array with surfaces having covalently attached amine groups (CovaLink NH modules) to which nucleic acid probes can be coupled using water soluble carbodiimides such as 1-ethyl-3-(3-dimethylaminopropyl)-carbodiimide as the condensation reagent.

The detection used in conjunction with the invention will depend on the nature of the label. Where a calorimetric or fluorescent label is used, visual inspection or an optical instrument will suffice; suitable instruments include, for example, the fluorescence microscope from Olympus (Lake Success, N.Y.), the Plate Reader device from BioTek Instruments (Winooski, Vt.), and the CCD (charge-coupled device) camera from Princeton Instruments (Princeton, N.J.). Where radioisotopes are used, detection can comprise such spatially sensitive detection devices as the Phosphor Imager device (Molecular Dynamics, Sunnyvale, Calif.), or can comprise separately detecting individual solid surfaces in a detection apparatus such as a gamma-counter or a liquid scintillation counter.

As was noted at the outset of the present specification, it is contemplated that one context in which the padlock probes set forth herein are preferably used is in the context of a microfluidics device that is designed specifically for moving small volumes of fluids through fluid exchange channels that connect various sorts of fluid chambers. In particular, such a device comprises a fluid chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the inventive device includes a reaction chamber wherein, for example, suitable means are employed for amplifying nucleic acid in the reaction chamber. The reaction chamber is comprised of any suitable material, as are all fluid chambers, such as, for example, glass, plastic, ceramic, or combinations thereof, and is connected to at least two fluid exchange channels for passaging material in and out of the reaction chamber. The reaction chamber preferably remains at a constant temperature of within about two degrees centigrade, wherein the temperature is between about 20° C. and 65° C., and alternatively can have adjustable temperatures as in accordance with the requisites of the reactions to take place therein. The reaction chamber can also be the site at which the detection methods described hereinabove take place. Preferably, the solid surface of the described method when the inventive method is employed in the context of a microfluidics device is a microparticle, more preferably a paramagnetic microparticle.

While this invention has been described with an emphasis upon preferred embodiments, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed:

1. A method for the detection of a second polynucleotide, comprising:

(A) providing a first polynucleotide, wherein the first polynucleotide comprises: a segment, the segment comprising the complement of at least the terminal four nucleotides of the 5' and 3' termini of the second polynucleotide such that the 3' and 5' termini of the second polynucleotide abut to each other upon hybridization of the first and second polynucleotides, wherein the first polynucleotide has a first ligand attached on one side of the segment and a first ligand attached on the other side of the segment;

(B) placing the first polynucleotide in contact with the second polynucleotide under hybridizing conditions;

(C) immobilizing the first polynucleotide by contacting with a solid surface comprising a second ligand that binds to the first ligands of the first polynucleotide; and (D) detecting any second polynucleotide immobilized in a complex with the first polynucleotide.

2. The method of claim 1, wherein the second polynucleotide includes a label or a third ligand, wherein the third ligand is recognized by a fourth ligand that includes a label.

3. The method of claim 2, further comprising joining the termini of the second polynucleotide of the first-second polynucleotide complex with a joining agent.

4. The method of claim 2, further comprising washing the first-second polynucleotide complex with a wash fluid, thereby removing unhybridized second polynucleotide.

5. The method of claim 3, wherein the first, second, third, or fourth ligand is biotin, streptavidin, an antigen, an antibody that recognizes the antigen, an amine, or hydrazine, wherein at least one ligand is bound to each of the first polynucleotide and solid surface, which ligands are the same or different; and the label is a radioisotope, a fluorescent dye, or a signal-generating enzyme.

6. The method of claim 3, wherein the second polynucleotide is a product of a nucleic acid amplification reaction.

7. The method of claim 3, wherein the first polynucleotide has multiple forms wherein each of such forms include different segments that are specific to the complements of at least the terminal four nucleotides of each of the 5' and 3' termini of different second polynucleotides.

8. The method of claim 7, wherein each form of the first polynucleotide is attached to a distinct location on the solid surface.

9. A method for the detection of a second polynucleotide, comprising:

(A) providing a first polynucleotide, wherein the first polynucleotide comprises:
  (i) a first ligand attached to each of its termini; and
  (ii) at least one first segment comprising the complement of at least the terminal four nucleotides of each of the 5' and 3' or the 3' and 5' termini of a first probe and a second probe, respectively;

(B) providing the first probe comprising a second segment located at one of its termini and having at least four nucleotides of the complement of the second polynucleotide;

(C) providing the second probe comprising a third segment located at one of its termini and having at least four nucleotides of the complement of the second polynucleotide, with the proviso that the second and third segments are different and are the complements of contiguous segments of the second polynucleotide;

(D) contacting the first polynucleotide with a solid surface or a solid surface comprising a second ligand that binds to the first ligands of the first polynucleotide, thereby immobilizing the first polynucleotide;

(E) contacting the first and second probes with a second polynucleotide under conditions that promote hybridization between complementary nucleic acids, forming a probe-second polynucleotide complex;

(F) joining the termini of the hybridized first and second probes of the probe-second polynucleotide complex with a joining agent;

(G) contacting the joined first and second probes with the first polynucleotide under conditions that promote hybridization between complementary nucleic acids, forming a probe-first polynucleotide complex;

(H) joining the termini of the hybridized first and second probes of the probe-first polynucleotide complex with a joining agent;

(I) washing the probe-first polynucleotide complex with a wash fluid, thereby removing unhybridized joined first and second probe; and (J) detecting the second polynucleotide by detecting a label or third ligand attached to the first or second probe, wherein the third ligand is recognized by a fourth ligand that includes a label.

10. The method of claim 10, wherein steps (E), (F), (G), and (H) are combined.

11. The method of claim 9, wherein a denaturation step is employed after step (H) after which steps (E), (F), (G), and (H) are repeated.

12. The method of claim 11, wherein the denaturation step after step (H) followed by steps (E), (F), (G), and (H) are repeated at least three times prior to exercising steps (I) and (J).

13. The method of claim 11, wherein the first, second, third, or fourth ligand is biotin, streptavidin, an antigen, an antibody that recognizes the antigen, amine, or hydrazine, wherein at least one ligand is bound to each of the first polynucleotide and solid surface, which ligands are the same or different; and wherein the label is a radioisotope, a fluorescent dye, or a signal-generating enzyme.

14. The method of claim 13, wherein the first or second probe, or fourth probe includes the label.

15. The method of claim 9, wherein the solid surface is a paramagnetic microparticle or wherein the solid surface is flexible and planar, such that a single solid surface is formed into a cylinder or a multiplicity of such solid surfaces are joined and formed into a cylinder.

16. The method of claim 9, wherein the second polynucleotide is a product of a nucleic acid amplification reaction.

17. The method of claim 9, wherein the first polynucleotide has multiple forms, wherein each of such forms include different first segments, and wherein the first and second probes also have multiple forms that include different second and third segments, respectively.

18. The method of claim 17, wherein the multiple forms of the first polynucleotide are immobilized on the solid surface, wherein the solid surface is one of a group of differentially labeled paramagnetic microparticles or is flexible and planar, such that a single solid surface is formed into a cylinder or a multiplicity of such solid surfaces are joined and formed into a cylinder.

19. A method for the combined amplification and detection of a polynucleotide comprising implementing a nucleic acid amplification of a polynucleotide and the method of claim 1, wherein the amplification and the method of claim 1 are implemented in the same reaction chamber.

20. A method for the combined amplification and detection of a polynucleotide comprising implementing a nucleic acid amplification of a polynucleotide and the method of claim 9, wherein the amplification and the method of claim 9 are implemented in the same reaction chamber.

* * * * *